United States Patent [19]

Hansen et al.

[11] Patent Number: 4,984,584
[45] Date of Patent: Jan. 15, 1991

[54] HIGH ELASTIC MODULUS BANDAGE

[75] Inventors: Paul E. Hansen, Lake Elmo; Christopher J. Libbey, St. Joseph, both of Minn.

[73] Assignee: Riker Laboratories, Inc., St. Paul, Minn.

[21] Appl. No.: 520,114

[22] Filed: May 8, 1990

Related U.S. Application Data

[63] Continuation of Ser. No. 443,012, Nov. 28, 1989, abandoned, which is a continuation of Ser. No. 206,565, Jun. 14, 1988, abandoned, which is a continuation-in-part of Ser. No. 186,675, Apr. 21, 1988, abandoned, which is a continuation of Ser. No. 3,779, Jan. 16, 1987, abandoned.

[51] Int. Cl.$^5$ .................. A61F 13/06; A61F 13/08; B32B 5/04; B68C 5/00
[52] U.S. Cl. .................................. 128/898; 54/82; 128/156; 128/165; 428/152; 428/287; 428/293; 428/295; 428/302
[58] Field of Search .................... 54/82; 128/156, 898; 428/152, 287, 293, 295, 302

[56] References Cited

U.S. PATENT DOCUMENTS

| 22,038 | 11/1858 | Solis | 428/239 |
| 2,740,402 | 4/1956 | Scholl | 128/156 |
| 3,575,782 | 4/1971 | Hansen | 425/465 |
| 4,349,020 | 9/1982 | Krikorian | 128/155 |
| 4,552,795 | 11/1985 | Hansen et al. | 428/110 |
| 4,606,338 | 8/1986 | Greenway et al. | 128/156 |

FOREIGN PATENT DOCUMENTS 0120117 10/1984 European Pat. Off.

OTHER PUBLICATIONS

Idea Submission Agreement (Bryan J. Hilbert).
3M Equine Bandaging Systems Product Brochure.

*Primary Examiner*—James C. Cannon
*Attorney, Agent, or Firm*—Donald M. Sell; Walter N. Kirn; Philip M. Goldman

[57] ABSTRACT

A high elastic modulus, cohesive bandage comprising partially extended spaced aligned elastic yarns sealed between two thin nonwoven fibrous webs by means of a polymeric binder is disclosed. The bandage provides joint support without imposing undue constriction. A method of supporting and/or providing compressive force to a mammalian limb including supporting suspensory ligaments and flexor tendons in the leg of a horse is also described.

10 Claims, 1 Drawing Sheet

HIGH ELASTIC MODULUS BANDAGE

CROSS REFERENCE TO RELATED APPLICATION

This application is a continuation of application U.S. Ser. No. 206,565, filed June 14, 1988, and now abandoned, which is a continuation-in-part of co-pending application U.S. Ser. No. 186,675 filed on Apr. 21, 1988, and now abandoned, which is a continuation of U.S. Ser. No. 003,779 filed Jan. 16, 1987, now abandoned.

BACKGROUND OF THE INVENTION

This invention relates to elastic shirred materials and the use thereof as a support bandage.

It is well recognized in the art that shirred fabrics can be made by stretching a sheet of rubber, holding it in a stretched condition, adhering a fabric to each side, and removing the restraining force to pucker or shirr. U.S. Pat. No. 22,038 describes material consisting of threads of India rubber stretched and bonded between two laminae of cloth and then permitted to retract, thereby causing puckering of the fabric to provide the desired shirred effect. U.S. Pat. No. 3,575,782 describes an elastic shirred web product consisting of partially extended spaced aligned elastic yarns sealed between two thin porous gathered non-woven fibrous webs, or between a web and a non-porous film, by means of a soft flexible polymeric coherent binder.

Elastic shirred web materials have been used in commercially available products such as Coban TM and Vetrap TM, both available from the Minnesota Mining and Manufacturing Company. Coban TM is sold for use as a support dressing on humans. Vetrap TM is sold for use on horses and other animals. Vetrap TM is used primarily for decorative purposes and as a rundown bandage. It is also used as a holding wrap for applying compresses, medicated pads and the like; and for providing support for injuries.

SUMMARY OF THE INVENTION

The present invention describes a cohesive elastic bandage comprising a series of spaced elastic yarns between coextensive thin non-woven fibrous cover webs, the bandage being uniformly impregnated throughout and bonded together in a unified structure with a polymeric binder having a basis weight at least equal to the basis weight of the cover webs. The yarns are maintained under tension in the resulting uniform structure. The yarns are from about 550 to about 1700 denier and are uniformly spaced at about 15 to 25 yarns (and preferably about 17 to 22 yarns) per inch of width with the proviso that the product of the denier times the number of yarns per inch of width is from about 10,000 to 25,000, preferably from about 10,000 to 15,000. The bandage is further characterized by having a ratio of $F_{125}/F_{50}$ of less than 10, and preferably less than 5, where $F_n$, an elastic modulus value, is the force required to elongate a test sample a certain percentage (n) beyond its relaxed length.

A method of supporting the suspensory ligaments and flexor tendons in the leg of a horse is also described.

The present invention also involves elastic shirred sheet material but has several advantages over that taught in the art. The material of the invention has a higher elastic modulus, is more cohesive and is more durable.

In one preferred form, the product of the invention has utility as an equine bandage. The bandage is durable enough to be used as a rundown bandage without the addition of rundown patches which are generally necessary when currently available bandages are used. Surprisingly, the higher elastic modulus of the bandage allows it to provide a high level of joint support without unduly constricting circulation.

DETAILED DESCRIPTION OF THE INVENTION

Figure 1:
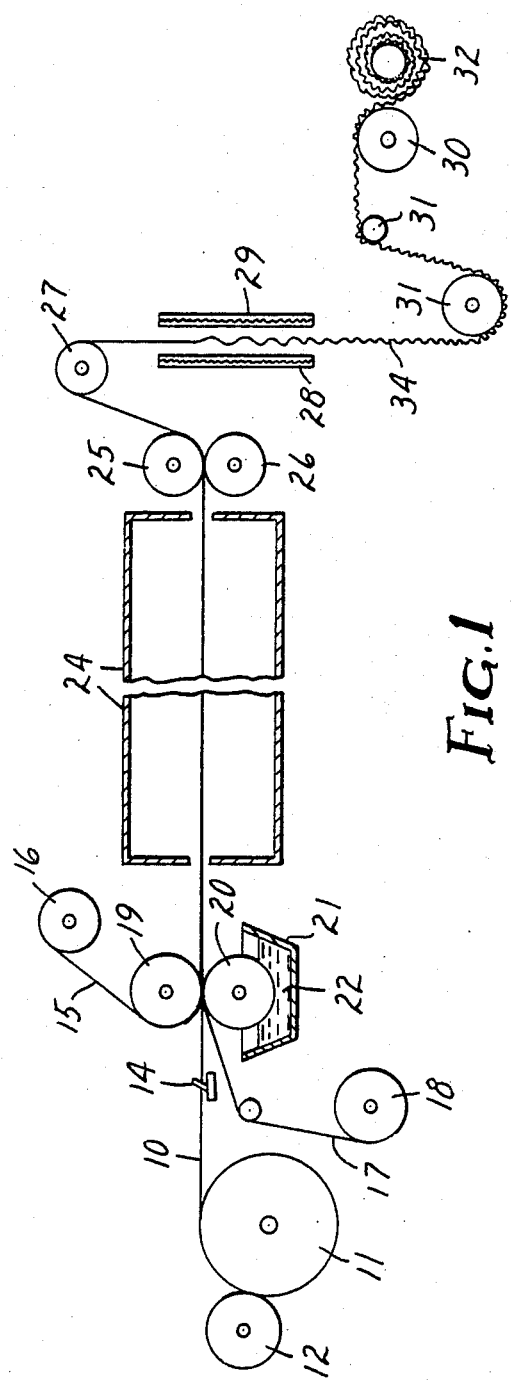
FIG. 1 is a schematic representation showing the manufacture of the elastic sheet material.

As shown in FIG. 1, elastic yarns 10 from a beam 11 are unwound under tension controlled by driven press roll 12 and through comb 14. Thin non-woven fibrous webs 15 and 17, from supply drums 16 and 18, respectively, or directly from the forming machine, if desired, are brought into contact with the yarns and with each other between rubber-covered squeeze roll 19 and knurled steel squeeze roll 20, the latter dipping into a pan 21 containing a fluid binder mixture 22 and depositing the binder mixture throughout the web 17. The composite web passes directly into a drying oven 24 and thence between pull drums 25 and 26. The web next passes around roll 27, between heating platens 28 and 29, around idler rolls 31 and surface winder roll 30, and is wound up to form stock roll 32.

Figure 2:
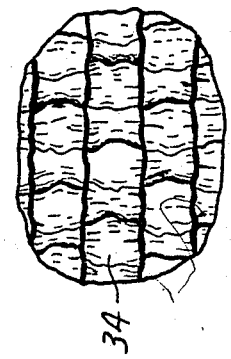
FIG. 2 is a representation in plan view of a portion of the product.

Squeeze rolls 19 and 20 rotate at a considerably greater surface speed than does beam 11, and the yarns 10 are accordingly stretched a corresponding amount. This stretch is maintained by operating pull drums 25 and 26 and turn-around drum 27 at approximately the same speed compared with rollers 19 and 20. Surface winder roll 30 and wind-up drum 32, however, are again operated at a slower speed to permit shrinkage of the web as it passes between the heater platens 28 and 29. The composite web 34, which is smooth as it reaches the roll 27, becomes increasingly puckered or shirred as it passes through the heating zone, the result being further indicated in FIG. 2.

The heat supplied by the platens 28 and 29 is sufficient to cause considerable fuming of the sheet material and to relax the structure sufficiently to permit the elastomeric yarns to retract and produce the desired degree of puckering or shirring as controlled by the speed of the surface winder roll. The temperature may be regulated by adjusting both the energy input to the platens and the distance between the platens and the web. In a typical installation for producing a finished web, the electrically heated platens are each 48 inches high, and are spaced between six and nine inches from the web. The platens are operated 600° F. at idle and 525° F. when the web is running. The duration of the heat treatment may be regulated, for a given length of platen, by adjusting the speed of travel of the web, sufficient time being provided to permit retraction of the web to the desired degree. The platens are maintained at a temperature sufficient to keep the web taut during the shrinking operation between rolls 27 and 30 at the speed indicated but not so high as to cause deterioration of the web as evidenced by excessive fuming and discoloration thereof. The length of the relaxed web after retraction will be within the range of about one-third to about two-thirds the fully extended length. The elastic yarns are initially stretched to a length of about three to five times (and preferably three to three and one-half times) their fully relaxed length (the ratio of stretched length to relaxed length of the yarns is referred to as the draw ratio), and are permitted to relax only partially during the puckering step. Nevertheless, the shirred product is dimensionally stable, the heat treatment serving to provide an effective degree of heat-setting or stabilizing, and neither shrinks nor expands when allowed to stand at normal temperatures and under no external stress; and it returns to such dimensions when first stretched and then permitted to retract.

The thin fibrous matts are conveniently prepared on a carding machine or on a "Rando-Webber" machine. Matts of polyester or rayon staple fibers or mixtures are preferred. The fibers are desirably of about 1.75 denier and about 1.5 inch in length, and the matt is about 0.25 to 0.50 oz./sq. yd. or about 5-10 lb. per 320 sq. yd. These very thin matts are fragile and flimsy, but show surprising strength when combined in composite structures of the type and in the manner hereinabove indicated. The matt as first formed is preferably reinforced by lightly treating it with a compatible bonding agent. As an example, the reinforced matt may consist of 75 parts by weight of polyester staple fibers and 25 parts of polyethyl acrylate, the latter being applied at the forming machine by saturating with a dilute emulsion of the polymer, removing the excess between squeeze rolls and drying in an oven.

Concentrated natural rubber latex is preferred as the impregnating and bonding or unifying medium. Other elastomers or blends of elastomers having similar properties may be used. The dried rubbery residue, although presenting a slightly tacky feel, does not adhere to the skin, but cohesively bonds to itself with sufficient force to hold the contacting layers together against reasonably high shearing stresses. The impregnating and bonding materials may be used without further modification, but will ordinarily be blended with pigments or other visual modifiers.

In an illustrative example, the yarns 10 are 700 denier spandex spaced 18 ends per inch of width and each of the webs 15 and 17 consists of a polyester matt (0.3 oz/ yd.$^2$). Centrifuged natural rubber latex at 61% concentration (available under the trade designation "GNL 200" from Goodyear Tire and Rubber Company) serves as the fluid binder mixture 22. In order to provide the desired elasticity, the spandex beam 11 is run at 41% of the line speed (rolls 19 and 20). To help insure good lamination at the desired draw ratio, the oven 24 and rolls 25, 26 and 27 are over-speeded 13% relative to the line speed. In order to allow the web to relax in the shrink tunnel (platens 28 and 29), rolls 30 and 32 are run at 45% of the line speed. The total draw ratio contributed by the tension of the elastic yarn on the beam and the further stretch resulting from the speed differential between beam 11 and rolls 19 and 20 is about 3.5. The resulting sheet material was slit into bandages 4 inches wide and 5 yards long (stretched dimensions). This material is referred to as Example 1 in the discussion below.

In one preferred method of the invention, a bandage of the invention is applied to the front leg of a horse in a series of FIG. 8's extending below the fetlock joint as low as the coronary band, and above the fetlock joint as high as the knee. This provides support for the suspensory ligaments and flexor tendons, thereby reducing the potential for injury due to hyperextension of the fetlock joint. The bandage is applied at about 50% of its usable stretch. Most preferably, three layers of FIG. 8's are employed and vertical splints which comprise folded lengths of the bandage of the invention are inserted between the first and second and second and third layers of the applied bandage. The splints are placed over the posterior part of the leg directly over the tendon and ligament structure.

The physical characteristics of the bandage of Example 1 of the invention were measured. The $F_n$ values measured as described below (except that three replicates instead of the stated five replicates were run) show that the bandage of Example 1 exhibits an $F_{125}/F_{50}$ value of less than five. The bandages of the invention are seen to exert a useful compression force in the usable range of 25% to 100% elongation while still maintaining the ability to stretch an additional 50% while in use without exerting an unduly high compressive force which could constrict circulation and cause physical damage to a horse's leg.

This performance has been borne out in university clinical trials and repeated field trials where horses, legs have been wrapped with the bandage of Example 1 by various trainers using varied techniques followed by normal race activity. The bandage has provided support without imposing undue constriction and has shown good durability during races. Specifically, when used at racing speed the bandage has been shown in some horses to reduce the drop of the fetlock joint, stabilize the stride and reduce distal limb vibration in the swing phase.

It is contemplated that the bandage of the invention would have utility in other mammals in addition to horses. For example, it is anticipated it could be used as a compressive and/or support bandage on humans, particularly in the field of sports medicine.

TENSILE AND ELONGATION MEASUREMENTS

This procedure uses stress-strain tester "MTS-810" available from Materials Testing Systems, Minneapolis, Minn., to determine $F_n$ modulus values. The $F_n$ modulus value is the force required to elongate the test specimen a certain percent (n) from the unstretched length. The machine conditions were set at a gauge length of 50 mm, a crosshead speed of 50 inches/min. Data was collected with a digital oscilloscope utilizing a twelve-second total sampling period. A 1" wide by 8" long sample was razor cut from a bandage. In order to minimize the incidence of jaw breaks, masking tape tabs were applied so that one tab was located in each jaw of the apparatus. The sample was clamped between the jaws, the crosshead was started and the stress plot was recorded, the $F_n$ values were calculated from the stress plot and the $F_{125}/F_{50}$ ratios were calculated. The $F_{125}$ and $F_{50}$ values used in computing $F_{125}/F_{50}$ values recited in the claims are the average of five independent determinations. This procedure is derived from ASTM D 882-80a, incorporated herein by reference.

What is claimed:

1. A cohesive bandage comprising a series of spaced elastic yarns between coextensive thin non-woven fibrous cover webs, the bandage being uniformly impregnated throughout and bonded together in a unified structure with a polymeric binder having a basis weight at least equal to the basis weight of the cover webs, said yarns being maintained under tension in said unified structure, and wherein said elastic yarns are from about 550 to about 1700 denier and are uniformly spaced at about 15 to 25 yarns per inch of width with the proviso that the product of the denier times the number of yarns per inch of width is from about 10,000 to about 25,000; said cohesive bandage being further characterized by the ratio of the elastic modulus $F_{125}$ value to the elastic modulus $F_{50}$ value being less than about 10.

2. The bandage of claim 1 wherein said elastic yarn is about 600 to 1,000 denier.

3. The bandage of claim 1 wherein said elastic yarn is uniformly spaced at about 17 to 22 yarns per inch of width.

4. The bandage of claim 1 wherein the product of the denier times the number of yarns per inch of width is about 10,000 to 15,000.

5. The bandage of claim 1 wherein said elastic yarn is about 700 denier and is uniformly spaced at 18 yarns per inch of width.

6. The bandage of claim 1 wherein said elastic yarn is about 1680 denier and is uniformly spaced at 18 yarns per inch of width.

7. The bandage of claim 1 wherein said polymeric binder comprises natural rubber latex.

8. The bandage of claim 1 wherein the ratio of the elastic modulus $F_{125}$ value to the elastic modulus $F_{50}$ value is less than about 5.

9. A method of supporting the suspensory ligaments and flexor tendons in the leg of a horse comprising applying a bandage of claim 1 to the leg.

10. A method of providing support and/or compressive force to a mammalian limb comprising applying a bandage of claim 1 to the limb in a manner to provide said support and/or compressive force.

* * * * *